(12) United States Patent
Pappu et al.

(10) Patent No.: US 11,656,212 B2
(45) Date of Patent: May 23, 2023

(54) SYSTEM AND METHOD FOR MEASURING TOTAL CHLORIDE CONTENT IN A PROCESS PRODUCT STREAM

(71) Applicant: JOHNSON MATTHEY PUBLIC LIMITED COMPANY, London (GB)

(72) Inventors: Sravan Pappu, Chicago, IL (US); Michelle Taylor Wilson, Stockton-on-Tees (GB)

(73) Assignee: Johnson Matthey Public Limited Company, London (GB)

(*) Notice: Subject to any disclaimer, the term of this patent is extended or adjusted under 35 U.S.C. 154(b) by 578 days.

(21) Appl. No.: 16/617,231

(22) PCT Filed: Jun. 4, 2018

(86) PCT No.: PCT/GB2018/051519
§ 371 (c)(1),
(2) Date: Nov. 26, 2019

(87) PCT Pub. No.: WO2018/224810
PCT Pub. Date: Dec. 13, 2018

(65) Prior Publication Data
US 2021/0132020 A1 May 6, 2021

Related U.S. Application Data

(60) Provisional application No. 62/515,707, filed on Jun. 6, 2017.

(30) Foreign Application Priority Data

Jun. 29, 2017 (GB) ...................................... 1710412

(51) Int. Cl.
*G01N 33/00* (2006.01)
*G01N 1/20* (2006.01)
(Continued)

(52) U.S. Cl.
CPC ....... *G01N 33/0049* (2013.01); *G01N 1/2035* (2013.01); *G01N 1/4022* (2013.01);
(Continued)

(58) Field of Classification Search
CPC ............. G01N 33/0049; G01N 1/2035; G01N 1/4022; G01N 33/0016; G01N 33/2835;
(Continued)

(56) References Cited

U.S. PATENT DOCUMENTS 3,001,917 A    12/1899   Scheirer
4,105,508 A     8/1978   Arod et al.
(Continued)

FOREIGN PATENT DOCUMENTS

CN    104931593 A    9/2015
EP      0316260 A2   5/1989
(Continued)

OTHER PUBLICATIONS

Efran, Mani: "Chloride Removal in Refineries: A review of catalytic removal of chlorides from refinery streams and a critique of current analytical techniques for estimating chloride content", Catalysis, Mar. 1, 2011, pp. 1-10, XP055505543.
(Continued)

*Primary Examiner* — Robert R Raevis
(74) *Attorney, Agent, or Firm* — BakerHostetler

(57) ABSTRACT

The present invention relates to a method and system for measuring total chloride content in a process product stream. In particular, the present invention relates to a method of measuring hydrogen chloride and organochloride content, in situ, for a gaseous refinery process product stream. This method allows for measurement of hydrogen chloride and organochloride content in a single test method, which allows for optimised performance and maintenance schedules for chloride guard beds used within the refinery process.

19 Claims, 1 Drawing Sheet

(51) Int. Cl.
    *G01N 1/40*        (2006.01)
    *G01N 33/28*      (2006.01)

(52) U.S. Cl.
    CPC ..... *G01N 33/0016* (2013.01); *G01N 33/2835* (2013.01); *G01N 2001/205* (2013.01)

(58) Field of Classification Search
    CPC ........... G01N 2001/205; G01N 1/2247; G01N 33/0036
    USPC ........ 250/288, 339.11–339.13, 576; 73/23.2, 73/31.05, 31.07; 422/83–98
    See application file for complete search history.

(56) References Cited

U.S. PATENT DOCUMENTS

| | | |
|---|---|---|
| 5,260,220 A | 11/1993 | Dougherty et al. |
| 2012/0142115 A1 | 6/2012 | Banks et al. |

FOREIGN PATENT DOCUMENTS

| | | |
|---|---|---|
| GB | 1553747 A | 9/1979 |
| WO | 0146683 A2 | 6/2001 |

OTHER PUBLICATIONS

PCT/GB2018/051519, International Search Report dated Oct. 10, 2018.
PCT/GB2018/051519, Written Opinion dated Oct. 10, 2018.
GB1710412.6, Search Report under Section 17(5) dated Mar. 29, 2018.
GB1809103.3, Search and Examination Report under Section 17 and 18(3) dated Dec. 4, 2018.

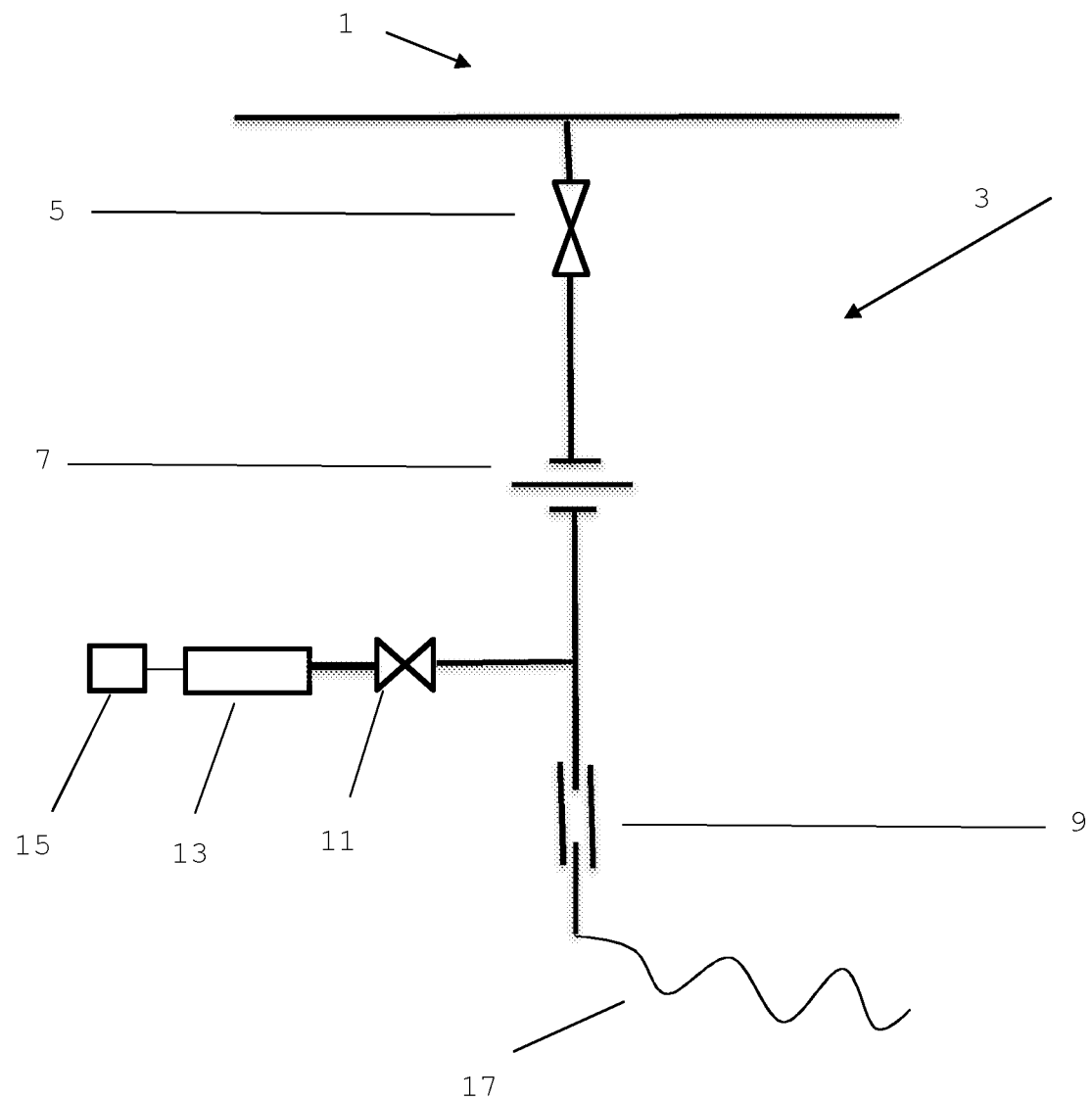

SYSTEM AND METHOD FOR MEASURING TOTAL CHLORIDE CONTENT IN A PROCESS PRODUCT STREAM

CROSS-REFERENCE TO RELATED APPLICATIONS

This application is the National Stage of International Patent Application No. PCT/GB2018/051519, filed Jun. 4, 2018, which claims priority to U.S. Provisional Patent Application No. 62/515,707, filed Jun. 6, 2017 and Great Britain Patent Application No. 1710412.6, filed Jun. 29, 2017, the entire disclosures of both of which are incorporated herein by reference for any and all purposes.

FIELD OF THE INVENTION

The present invention relates to system and method for measuring total chloride content in a process product stream. In particular, but not exclusively, the present invention relates a method of measuring both hydrogen chloride and organochloride content, in situ, for a gaseous refinery process product stream. This method allows for measurement of hydrogen chloride and organochlorides in a single test method, which allows for optimised performance and maintenance schedules for chloride guard beds used within the refinery process.

BACKGROUND

Chlorides are typically introduced into the refinery process plant in two ways. Firstly, some crude oil sources can bring both inorganic and organic chloride materials into the refinery process as part of the initial refinery feedstock. Generally, well known desalter processes are used to remove inorganic chlorides, such as hydrogen chloride and chloride salts, from this initial feedstock stream to prevent corrosion and fouling of downstream catalytic materials. The identification and removal of organochlorides is not commonly performed at this stage of the refinery process, and so organochlorides may be present in the product stream downstream of any such desalter. Secondly, chloride is commonly introduced to the refinery process at the point of the Catalytic Reforming Unit (CRU). In use, chloride is injected into the CRU and adsorbed onto the catalyst to provide the acid function necessary for optimal desired product conversion and reaction selectivity. These injected chlorides, however, are not permanently bound to the catalyst in the CRU and migrate into the resultant product stream and therein flow downstream of the CRU through the further steps of the refinery process. This is the most common way that hydrogen chloride will be introduced to the process product stream. The chloride content of the process product stream can, therefore, comprise both hydrogen chloride, often referred to as inorganic chloride in the field, (HCl), and organochlorides, (RCl).

The negative effects of HCl in downstream operations can include corrosion of austenitic stainless steels, ammonium chloride salting, pressure drop issues, and more general corrosion of downstream piping and other equipment. As such, the employment of HCl adsorbent or absorbent materials is used to avoid these effects; these materials are typically present in a chloride guard bed. However, the presence of organochlorides in the product stream means that hydrochloric acid can be produced downstream in the refinery process unexpectedly, for example in the hydrotreating or reforming reactors, and the acid then accumulates in condensing regions of the refinery. Therefore, damage can result due to unexpected concentrations of chlorides which cannot be effectively neutralized, even when HCl chloride guards have been employed in the process. As such, removal of organic chlorides (generically referred to as RCl) from the product stream is also important as they will contribute, upon conversion to HCl, to a variety of downstream issues. Two of the most commonly reported issues relating to organochlorides in refinery processes are:

1) $NH_4Cl$ plugging in hydrotreaters and stabilizer towers, and
2) Chloride stress corrosion cracking of stainless steel piping and exchangers.

In addition, any organochlorides present in the product stream may cause problems for downstream catalyst poisoning and final product specification. For example, catalysts based on nickel, copper and palladium are very susceptible to rapid deactivation by chloride ions. Alternatively, end users may require that final refinery products are free of any chloride content, for example where the product is to be used as a fuel.

Having consideration of the problems associated with the presence of chlorides in the product streams of a refinery process, there is a clear need for the monitoring and removal of both inorganic and organochloride species (i.e. HCl and RCl).

At present most refinery operations concentrate on removal of HCl only, meaning that problems associated with the presence of organochlorides are not overcome. HCl may be removed by a HCl-only chloride guard; but such chloride guards can also result in the creation of organochlorides, particularly where acidified chloride guards are employed. However, methods of total chloride removal (i.e. both HCl and RCl) to protect the refinery process and plant equipment from the disadvantages highlighted above are known, utilising the use of a total chloride guard system. A total chloride guard system typically utilises a mixture of catalyst(s) materials and molecular sieves. Usually a material capable of removing HCl will be employed in a first process bed, and a material capable of removing RCl will be employed in a separate second process bed downstream of the first process bed. However, for optimal performance of these total chloride guard systems, it is important that the materials contained in the beds are replenished as they become saturated with HCl and RCl materials and can no longer function, or do not function to a required degree. Typically, the performance of both types of chloride guard is assessed by measuring chloride breakthrough, in the form of HCl only, downstream of the chloride guard.

Currently, even where refineries employ chloride guard technology (for either HCl only or combined HCl and RCl removal), they do not have the ability to evaluate adequately the performance of their chloride guard beds. While inorganic chloride (HCl) monitoring is well understood, organochloride (RCl) and total chloride contents are typically not measured, which comes at a significant cost to downstream processing and equipment. As a result, many refiners only measure for HCl content in product streams, which does not identify RCl content, which can originate from the introduction of chloride to the CRU or be created by an acidified chloride guard. This results in corrosion and fouling downstream of the chloride guard without warning for the refiner. Therefore, it is very important to have a methodology that can adequately detect and quantify both inorganic and organic chlorides in a refinery product stream. At present, process plant operators may utilise HCl test methods, such as via Draeger™ tubes for HCl measurement of gas and/or liquid systems, in situ, on the refinery process site. However, such methods do not test for the presence of organochlorides, or provide total chloride content measurements of the product streams analysed. Such methods are therefore deemed inadequate as they do not take into account the presence of RCl materials. In consequence, the methods cannot be relied upon as a means of, for example, estimating when a chloride guard may need to be replenished (prior to chloride breakthrough in downstream product streams), or for achieving optimal process design in relation to the amount of HCl versus RCl removal material to be used in a total (combined HCl and RCl) chloride guard system.

Alternatively, process plant operators may remove sample material from the process gas and/or liquid product stream and these removed samples can then be sent for analysis, off site, via analytical laboratories. In this case the most common method of sample analysis is by flame ionisation chromatography for RCl, and potentiometric analysis for HCl. However, such analysis suffers from potential interference from other halogen containing compounds, such as bromides and fluorides, and also from sulphur species, which can result in a false higher measurement. The employment of such methods therefore, often leads to the overestimation of total chlorides present, meaning that chloride guard materials are changed more often than necessary, resulting in needless maintenance and downtime for the process plant. In addition, the obtaining of data from such off site analysis may take many hours, or even days, to return to the process plant operator, and therefore the information is out of date, and no longer represents the current operating conditions of the refinery process.

Preferred embodiments of the present invention seek to overcome one or more of the above disadvantages of the prior art. In particular, preferred embodiments of the present invention seek to provide an improved method for testing for the presence of total chloride content, in situ, such that the refiner/process plant operator is able to minimise undesirable plant downtime and ensure maximum capture of both inorganic and organic chlorides by the chloride guard to avoid the problems highlighted above. In addition, a system suitable for use in such a method is provided.

DEFINITIONS

By "HCl" it is meant hydrogen chloride, also referred to as inorganic chloride in the art.

By "RCl" it is meant any organochloride material.

By "total chlorides" it is meant the total concentration of chloride present in the form of HCl and RCl. Preferably the amount of RCl is expressed as "HCl equivalents", for example, where 3 ppmv of a tri-chloride organochloride material is present this may be expressed as 9 ppmv of equivalent HCl.

Use of the term "before" relates to the relevant upstream process step, and use of the term "after" relates to the relevant downstream process step.

By "in situ" it is meant on the process plant of interest, proximal to where the sample to be tested has been removed, such that the sample is not removed off site for testing to be performed.

The term "chloride guard" is intended to mean both a HCl-only chloride guard and also a HCl and RCl total chlorides chloride guard system, depending on the needs of the process.

The abbreviation "ppmv" stands for parts per million by volume.

SUMMARY OF INVENTION

According to a first aspect of the invention, there is provided a system for use in measuring total chloride content in situ on a process product stream.

The process product stream may be any stream containing chloride and in particular may be a stream upstream or downstream of a desalter, a chloride guard, a CRU or chloride-sensitive equipment. The chloride guard may comprise one or more chloride adsorbents disposed in one or more adsorbent vessels. The system may be also used between adsorbent vessels.

Preferably the system comprises a sample port. One or more sample ports may be present. Most preferably said one or more sample ports are permanently incorporated in to the process plant infrastructure to conveniently allow access to the process product stream. The provision of a permanently incorporated sample port allows for greater user safety when removing a product stream sample. Most preferably each sample port suitably comprises a valve, such that the sample port is in fluid communication with the process plant product stream flow via the valve. In this embodiment, the permanent incorporation of the one or more sample ports can be suitably achieved via the valve.

The one or more sample ports may be provided at any point in the process plant infrastructure, where measurement of total chloride content may be useful, in particular the system may comprise one or more sample ports in the locations identified below, in relation to the method step of removal of sample.

More especially, the system may comprise providing the one or more sample ports downstream of the CRU, and upstream of the chloride guard, such a system is particularly suited to use in a refinery process. Alternatively, the system may comprise providing the one or more sample ports upstream of any chloride-sensitive equipment.

Preferably the one or more sample ports comprise a restriction valve, to prevent back flow of the removed process product stream. More preferably the restriction valve allows for a controlled amount of process product stream to be removed from the process product stream.

Additionally, or alternatively, the one or more sample ports comprises a needle value. This advantageously allows a relatively small amount of product stream to be removed from the process product stream such that the quantity of sample to be tested removed is of an amount suitable for testing.

In addition, the one or more sample ports may comprise a vent. Preferably the vent is in the form of an open ended pipe, and more preferably an open ended flexible pipe. Said vent will allow for pressure release to ensure the safety of a user when the test method is performed in situ, alongside the process to be tested. This is an important safety feature of the system, especially where use of the system is at elevated pressure and temperature. Preferably, the vent is provided in the form of an open ended flexible pipe, the distal end of which may be directed such that any product stream sample ejected from the vent is sufficiently distanced from a user when the system is in use.

Additionally, or alternatively, the one or more sample ports comprise an isolation valve. This allows the flow of product stream into the sample port be switched off and on, i.e. product stream can be prevented or allowed to enter the sample port at the discretion of an operator. This is particularly preferred where the sample port is provided permanently incorporated in to the process plant infrastructure, so that the process product stream may only flow through the sample port when the test method, described below, is to be performed.

Preferably, the system comprises a chloride test apparatus. Suitably the chloride test apparatus is able to quantifiably measure the chloride content of a product stream sample to be tested, in accordance with the method described below. The chloride test apparatus can be provided by any known means. However, due to the in situ nature of the present system, the HCl chloride test apparatus must be suitable for use in situ. Suitable chloride test apparatus includes known chemical containing test tubes, pH indicators etc. Preferably the chloride test apparatus is of a suitable size to be considered hand-held. In some systems it is preferable that the chloride test apparatus is portable. In some preferred embodiments the chloride test apparatus is designed for single use.

Preferably the system comprises a chloride test apparatus which is removably-connected to the one or more sample ports via a connector. Suitably, the connector may be permanently fixed to the sample port. In use, the connector allows the product stream sample to flow from the sample port in to the chloride test apparatus. As such, the connector is provided with a first proximal sample port engagement end, and a second distal chloride test apparatus engagement end. Preferably the connector is provided by a flexible tube. Most preferably, the second distal chloride test apparatus engagement end of the connector will be removably-connected to the chloride test apparatus, such that the chloride test apparatus can be easily attached and detached at the start and end of the test method. This is advantageous where the HCl chloride test apparatus is a "single use" nature, and will require to be removed and replaced.

The engagement between the connector and the chloride test apparatus can be via any known means, however, a push fit engagement is preferred due to the associated ease of assembly.

Preferably, the system chloride test apparatus comprises a HCl chloride test apparatus, with a RCl conversion means and a HCl equivalents chloride test apparatus, arranged in series. Alternatively, the system may comprise a HCl chloride test apparatus, in parallel to a RCl conversion means and a HCl equivalents chloride test. In the latter case it is preferred that the system comprise two or more sample ports, and that the sample ports are spaced relatively close to one another, such that when in use an operator is able to perform the method, described below, without having to relocate to a different geographical position in the process plant.

Suitably the chloride test apparatus RCl conversion means can be achieved by any known apparatus. Suitably, the conversion means contains a catalytic material which converts RCl to HCl equivalents. As such, the conversion means is preferably a catalytic RCl conversion means.

It will be understood by the skilled person that the chloride test apparatus HCl chloride test apparatus and HCl equivalents chloride apparatus for use in the present system may be of the same type, or may be of a different type. It is preferred that both the HCl chloride test apparatus and the HCl equivalents chloride test apparatus are of the same type.

Additionally, the system may comprise a pump or aspirator. Preferably the system comprises an aspirator, and most preferably this is removably-connected to the chloride test apparatus. The pump or aspirator is employed to draw a known volume of sample product stream through the chloride test apparatus, suitable aspirators are known in the art.

Additionally, the system may optionally comprise a dehumidifier. Where the chloride test apparatus is sensitive to humidity the inclusion of a dehumidifier is particularly preferred. Known HCl chloride test apparatus suitable for use in refinery processes typically operate in a humidity range of 0-80% relative humidity at 20° C., and so use of a dehumidifier can be assessed on actual need based on the process conditions and HCl chloride test apparatus selected for use in the system.

According to a second aspect of the invention, there is provided a method for in situ measuring the total chloride content of a process product stream sample, comprising the steps of:
1) removing a sample to be tested from a product stream to provide a product stream sample,
2) analysing the product stream sample to measure the HCl content thereof,
3) converting any RCl in said product stream sample to produce HCl equivalents,
4) analysing the HCl equivalents produced in step 3) to measure the HCl equivalents content thereof,
5) calculating the total chloride content of the product stream sample based on the sum of the HCl and HCl equivalents content measurements of steps 2) and 4).

Most conveniently, the method is performed utilising a system as described above.

The method is particularly suitable for use in refinery processes. However, the method may be suitable for use in other processes where the monitoring of total chlorides in the product stream is desirable, for example, where equipment corrosion, or protection of downstream catalysts from chloride materials is advantageous. More especially, the method will be particularly useful in processes where chloride guards are employed and optimisation of the same alongside total chloride monitoring is desirable.

The product stream may be in the form of a gas or liquid. Preferably the product stream is gaseous.

Suitably, especially in the case of a refinery process, the method comprises performing step 1) after the introduction of the feedstock. This will allow the total chloride content of the feedstock to be appreciated prior to any other processing steps having taken place. This would allow the refiner to assess whether the feedstock required optional initial processing steps and process the feedstock product stream in the most effective manner.

Additionally, or alternatively, in the case of a refinery process, the method comprises performing step 1) after a desalter. This would allow for the refiner to measure any HCl eluting from the desalter, which would indicate that the desalter was not performing HCl removal adequately. Additionally, such a method would also identify any RCl which may require subsequent removal downstream in the process.

Additionally, or alternatively, and most preferably in the case of a refinery process, the method comprises performing step 1) after the CRU. This would allow the refiner to calculate the presence of both HCl and RCl which may have entered the product stream due to injection of chlorides into the CRU. Measurement of both RCl and HCl chloride content at this stage of the process is particularly advantageous, since it allows for the refiner to optimise the design of the downstream chloride guard, for example, where organochloride (RCl) levels are relatively high on elution from the CRU, the refiner can modify a chloride guard system to employ a greater level of RCl removal material versus the level of HCl removal material. Optimisation of the chloride guard will result in less maintenance and downtime for the process plant, as well as cost savings in relation to only utilising as much HCl and RCl removal material as is required. When using existing test methods for HCl content only, such process optimisation is not realised.

Additionally, or alternatively, preferably the method comprises performing step 1) before or after the chloride guard. Where the product stream sample to be tested is removed downstream of the chloride guard the operator is, for example, able to access whether the chlorine guard is performing its function adequately, if additional chloride removal is required as an optional processing step, or if the chloride guard requires immediate maintenance. For these reasons a method comprising performing step 1) downstream of the chloride guard may be particularly preferred.

Additionally, or alternatively, the method may comprise performing step 1) before or after any sensitive equipment. For example, the sample to be tested may be taken upstream of a sensitive catalyst bed, where the presence of chlorides would be detrimental to the performance of that equipment. In some processes the presence of unacceptably high levels of chloride being identified prior to the sensitive equipment would allow the refiner/operator to adjust the processing steps to protect the sensitive equipment as necessary. Alternatively, the monitoring of the chloride content entering or exiting a sensitive equipment may allow the refiner/user to better assess the need for maintenance of the sensitive equipment. A method comprising performing step 1) before or after sensitive equipment may be particularly preferred in a refinery process.

Additionally, or alternatively, the method comprises performing step 1) before final product discharge or storage. The removal of a product stream sample at, or immediately upstream of, the final product discharge from a process or final product storage may be advantageous, for example, for assessing whether a final product stream contains acceptably low levels of chlorides for its intended end use.

Preferably the method comprises performing step 1) removing of a sample to be tested from a product stream to provide a product stream sample via a sample port. The features of the sample port are disclosed above in relation to the system, as the system is suitable for use in performing the method provided herewith.

Suitably each sample port of the present method comprises a valve permanently incorporated in to the process infrastructure. As such, preferably step 1) of the method comprises removing of a sample to be tested from a product stream to provide a product stream sample via a valve in the sample port, which allows a portion of process product stream to flow out of the main process product stream.

Preferably the method comprises recording the volume of the product stream sample being subjected to the test method. This allows for data from the test method to be expressed in terms of "by volume" which is particularly useful. Recording of the volume of test sample may suitably be achieved via a sample port restriction valve, which allows for a controlled amount of process product stream to be removed from the process product stream, such that a known (and hence recorded) volume of product stream sample is provided in step 1). Alternatively, the volume of product stream sample subjected to the test method can be recorded via the chloride test apparatus, as described further below, or by some other means; in this case the step of recording the volume of the product stream sample being subjected to the test method is a distinct and additional step to method step 1).

Preferably the method is performed using a system wherein the sample port includes a vent, to ensure the safety of the user when the test method is in use. As such, preferably the method comprises an initial step of positioning the vent so as to direct any release through the vent in a direction away from the user, and most preferably to direct any release downwind of a user.

As described above, it is preferable that the chloride test apparatus is designed for a single use, and in this embodiment the sample port preferably comprises an isolation valve. Therefore, it may be preferable that the method include the step of opening a sample port isolation value as part of (or prior to) step 1) of the method. The method may also include the step of closing the sample port isolation value.

The method necessarily employs a chloride test apparatus, as described above, to perform method steps 2), 3) and 4).

Preferably, the method provides a quantitative measure of HCl content of between 0.05 ppmv and 50 ppmv, more preferably between 0.2 and 40 ppmv. As such, the HCl chloride test apparatus is selected to achieve this end. Such a method is particularly suited to use in a refinery process; in other processes the content of hydrogen chloride may vary and the selection of appropriate HCl chloride test apparatus may correspondingly vary.

Preferably, the method provides a quantitative measure of HCl equivalents between 0.05 ppmv and 50 ppmv, more preferably between 0.2 and 40 ppmv. As such, the HCl equivalents chloride test apparatus is selected to achieve this end.

Such a method is particular suited to use in a refinery process; in other processes the content of organochloride may vary and the selection of appropriate RCl chloride test apparatus may correspondingly vary.

Suitably, for example, where the chloride test apparatus utilised in the method is designed for a single use, the method may comprise the optional steps of attaching a chloride test apparatus, prior to performing the test method. Similarly, the method may preferably comprise the step of detaching a chloride test apparatus, at the end of the test method. Where a removable/single use chloride test apparatus is utilised in the method, user safety is enhanced where the sample port comprises an isolation valve. Therefore, the method may preferably comprise the following steps:
1) providing a sample port comprising an isolation valve, and attaching a chloride test apparatus to said sample port,
2) removing a sample to be tested from a product stream to provide a product stream sample via said sample port comprising the step of opening an isolation value, and subsequently closing the isolation value once the product stream sample has been removed,
3) analysing the product stream sample to measure the HCl content thereof,
4) converting any RCl in said product stream sample to produce HCl equivalents,
5) analysing the HCl equivalents produced in step 4) to measure the HCl equivalents content of the RCl content in the sample, and
6) calculating total chloride content based on the sum of the HCl and HCl equivalents content measurements of steps 3) and 5) to provide a total chloride content measurement.

By converting RCl to HCl equivalents, the present method allows for the calculation of RCl, and total chloride content, to be performed conveniently in situ. One advantage of this method is that it is performed in situ alongside the process being performed and in real time. Hitherto, methods of calculating the RCl content of a product stream were not suitable for use in methods performed in situ. Once the RCl contents of the sample have been converted to HCl equivalents, the HCl equivalents can then be measured, in accordance with step 5) of the method.

Most preferably, the method comprises the product stream sample being subjected to step 3) and then sequentially progressing to steps 4) and 5) of the method (for the conversion of RCl to HCl via the RCl to HCl conversion means), such that the calculation of HCl equivalents from RCl is performed on the same product stream sample removed in step 2) in series. However, in an alternative method, two (or more) samples can be taken in parallel in step 2), the first parallel sample is subjected to step 3), and the second parallel sample is subject to steps 4) and 5).

Once a calculation of both the HCl content in step 3) and the HCl equivalents content of the RCl in step 5) has been performed, calculation of the total chloride content of the sample based on the sum of the HCl content calculations of steps 3) and 5) can be derived, as in step 6) of the method.

In addition, as will be appreciated from the description above, the amount of HCl and HCl equivalents resulting from RCl will be determined from the performance of the method. This is advantageous, as alluded to above, in relation to optimising total chloride guard systems, where removal of organochlorides and inorganic chloride may be achieved independently.

Where the method comprises the step of removing the sample to be tested via a sample port, the means for calculating the HCl contents in both step 3) and step 5) may be directly, removably-connected to the sample port. Clearly, where the method steps of 3), and 4) in combination with 5) are performed in parallel, the means for calculating the HCl content in step 3) can be removably-connected to one sample port, and the means for calculating the HCl equivalents content in step 5) can be removably-connected to a parallel sample port. However, more preferably, the method steps 1-6) are performed on a single sample to be tested in series. As such the method may comprise the following steps:

1) providing a sample port (optionally comprising an isolation valve), and attaching a chloride test apparatus and attaching a HCl equivalents test apparatus to said sample port,
2) removing a sample to be tested from a product stream to provide a product stream sample via a sample port (optionally comprising the step of opening the isolation valve, and subsequently closing the isolation value once the product stream sample has been removed),
3) analysing the product stream sample to measure the HCl content thereof,
4) subsequently converting any RCl in said product stream sample from step 3) to produce HCl equivalents,
5) analysing the HCl equivalents produced in step 4) to measure the HCl equivalents of the RCl content in the sample,
6) calculating the total chloride content based on the sum of the HCl and HCl equivalents content measurements of steps 3) and 5) to provide a total chloride content measurement.

Preferably the method is performed at a pressure not exceeding 100 bar G, as above this pressure level damage to the chloride test apparatus may occur and the accuracy of the measurement derived from the chloride test apparatus may also be detrimentally effected.

It is envisaged that in some embodiments of performing the method the product stream may leave the process plant under sufficient pressure that the removed product stream sample is self-propelling through the sample port and chloride test apparatus. However, alternatively, and more preferably, the method comprises reducing the pressure of the sample product stream to approximately ambient pressure level. This reduction in pressure has safety benefits and may be achieved by a naturally occurring pressure drop between the process plant and the sample port, described above, or a known pressure regulator means may be employed. Therefore, optionally, and most preferably when the product stream sample is not of sufficient pressure to self-propel through the apparatus used to perform the method, the method includes the using a pump or aspirator to draw the product stream sample of step 1). As described above in relation to the system, preferably an aspirator is used as is common for use in HCl chloride test apparatus.

Optionally, the method may further comprise the step of passing the sample product stream through a dehumidifier. Where the chloride test apparatus is sensitive to humidity the inclusion of this step is particularly preferred. Known HCl chloride test apparatus suitable for use in the present method typically operates in a humidity range of 0-80% relative humidity at 20° C., and so use of a dehumidifier in the test method is particularly preferred in process where the product stream product will have a humidity outside of this operating range.

It will be appreciated that features described in relation to one aspect of the invention may be equally applicable in another aspect of the invention. For example, features described in relation to the system aspect of the invention, may be equally applicable to the method aspect of the invention, and vice versa.

DESCRIPTION OF THE DRAWINGS

Embodiments of the present invention will now be described, by way of example, and not in any limitative sense, with reference to the accompanying drawings, of which:

FIG. 1 is a schematic of the features of the system, in situ on a process plant.

DETAILED DESCRIPTION

With reference to the attached drawing an in situ method of measuring total chloride content in a refinery process product stream is provided, utilising a system in accordance with one embodiment of the present invention, and is described in more detail herewith.

Removal of a gaseous product stream sample to be tested from a product stream from a process plant (1) product stream flow is achieved via the sample port (3). The sample removal occurs downstream of a refinery CRU (not shown), and upstream of a chloride guard (not shown). Hence a product stream sample to be tested for total chloride content is provided.

The sample port (3) comprises a valve (5) which is permanently in place within the refinery process plant system. When the refiner/operator wishes to measure the total chloride content of the product steam within the process product stream the valve (5) is set to open and a controlled flow of product stream is allowed to leave the process plant (1) via the valve (5), to provide the product steam sample. The valve (5) will only allow product stream to flow out of the process plant (1), and back flow is prevented.

Control of sample product stream flow is achieved by virtue of a restriction valve (7), in association with the initial valve (5), so that the volume of sample product stream can be restricted so as not to overload the downstream chloride test apparatus (in some cases this will be used in combination with a needle valve (not shown) to ensure only a very small amount of product stream sample enters the chloride test apparatus (13)).

The sample port (3) is also provided with a vent (9) to ensure user safety when the refiner performs the method. The vent is provided with a flexible tube (17) which will release product from the sample port assembly if the pressure exceeds a pre-determined safe limit. The flexible tube (17) is positioned and directed so that it vents to a safe area (e.g. downwind of the refiner performing the method).

In the present example the sample port (3) also comprises an isolation valve (11), which is positioned such that the flow of product stream out of the sample port can be switched off and on immediately prior to the sample entering the chloride test apparatus (13). This allows for a single use chloride test apparatus to be conveniently used, where the chloride test apparatus can be attached to the isolation valve via a push fit connector, and subsequently the isolation valve (11) opened for the duration of the chloride measurement method being performed via the chloride test apparatus. Following performance of calculation of the necessary HCl and HCl equivalents content, the isolation valve (11) can be closed for safe removal of the single use chloride test apparatus (13).

In the present example the method is performed with the HCl measurement and RCl measurement, as HCl equivalents, derived from analysing the same single sample product stream, in series. The product stream sample to be analysed is drawn through the chloride test apparatus (13) by use of an aspirator (15). Within the chloride test apparatus (13) the sample to be tested first passes through a HCl chloride test apparatus, then passes through a RCl to HCl conversion means and then subsequently passes through a HCl equivalents chloride test apparatus. Hence, steps 3, 4 and 5 of the method (as described above) are conducted in series. The HCl content measurements are displayed visibly on each of the HCl and HCl equivalents chloride test apparatus in terms of ppm.

In the present example the pressure of the sample product stream leaving the process plant has dropped to an ambient level as it has passed though the sample port (3).

Therefore, it is necessary to use an aspirator (15) to draw the product stream sample through the chloride test apparatus (13). The aspirator (15) includes a visual indicator to monitor and demonstrate the volume of gas aspirated and hence passing through the chloride test apparatus (13). As the aspirator (15) draws a known volume of product stream sample through the chloride test apparatus (13), the chloride and chloride equivalents content of the sample tested can be expressed in terms of ppmv. It should be appreciated that the results obtained by the chloride test apparatus are dependent upon the volume of product stream sample entering the chloride test apparatus, and so expressing the chloride content in terms of ppmv is appropriate (as is ordinary in the art for measuring HCl only). The refiner/operator is able to calculate the total chloride content of the sample simply by adding the two displayed measurements together, i.e. the initial HCl chloride content measurement displayed is added to the RCl HCl chloride equivalents content measurement displayed, to provide a total chloride content measurement. Having obtained both the HCl and RCl HCl equivalents content in ppmv the operator can then extrapolate the information to calculate the levels of chloride and organochloride departing the CRU and entering the chloride guard. As such, the process plant operator is able to modify and optimise the chloride guard for maximum removal of both HCl and RCl. Furthermore, the operator is able to more accurately monitor the level of chlorides (HCl and RCl) entering the chloride guard and so can better estimate the time at which the chloride guard will require maintenance.

In the present example the chloride test apparatus (13), which comprises first HCl chloride test apparatus, and the subsequent RCl to HCl conversion means and second HCl equivalents chloride test apparatus, is removably-connected to the sample port (3), via a connector in the form of an inert flexible tube, positioned between the isolation valve (11) and the chloride test apparatus (13). The distal end of the connector is removably-connected to the chloride test apparatus (13), such that the chloride test apparatus (13) can be easily attached and detached, at the start and end of each test method, as the chloride test apparatus (13) is designed for a single use.

Example 1

To demonstrate the utility of the in situ method provided herewith for measuring chloride content, an experimental refinery process test chloride breakthrough rig was set up. The rig included a 60 ml CRU bed, which was loaded with an appropriate catalyst and inserted into a glass reactor to provide an experimental CRU. The CRU was connected to an upstream reactor into which HCl and RCl may be introduced independently or simultaneously. Tertiary butyl chloride (TBC), a representative organochloride, was fed into the reactor, via injection in to a representative product gas stream, at differing concentrations and the product gas stream downstream of the CRU was sampled and analysed in situ for ascertaining the content of RCl and HCl present in the product stream sample. A HCl measurement chloride test apparatus was utilised to test for the presence of HCl, and the same type of chloride test apparatus, but with a preceding catalytic RCl conversion means, was utilised to test for the presence of RCl HCl equivalents. The results obtained from using the in-situ method of measuring total chloride content were compared against the measurements obtained from off-site analysis of a similarly removed sample by gas chromatography (GC).

Results

TABLE 1

| Target concentration of RCl (ppm) from TBC feed | RCl content measured by GC | HCl concentration (ppm) measured by HCl test apparatus only | HCl concentrations (ppm) measured by HCL test apparatus proceeded by RCl conversion means |
| --- | --- | --- | --- |
| 100 | 98.7 | 4 | 90 |
| 300 | 288.5 | 4.5 | 300 |
| 500 | 549.9 | 5 | 520 |
| 800 | 823 | 5.5 | 700 |

It can be seen from Example 1 that RCl has an effect on the HCl test apparatus used. Where an RCl conversion means is used in combination with a HCl test apparatus then the most accurate measurement of RCl as HCl equivalents is obtained. If the refiner/operator were to rely on current HCl only measurement methods, the levels of RCl present in the sample product stream would be overlooked and downstream process plant protection from these materials could not be optimised. It is noted that HCl is detected in the HCl test apparatus where no RCl conversion means is employed, this is believed to be the result of some of the RCl introduced to the CRU converting to HCl. Total chloride content can be easily calculated by the sum of the measurement obtained from the HCL test apparatus only measurement, and the measurement obtained from the RCl conversion means in combination with the HCl test apparatus.

It will be appreciated by persons skilled in the art that the above embodiments have been described by way of example only, and not in any limitative sense, and that various alterations and modifications are possible without departure from the scope of the invention as defined by the appended claims, for example, in the system described a needle valve may be utilised in addition to a regulator valve, or an alternative pressure release system may be employed where no technical difficulty is apparent.

The invention claimed is:

1. A system for measuring total chloride content in situ in a process product stream, the system comprising a sample port comprising an isolation valve, a chloride test apparatus and a connector connecting the valve and the chloride test apparatus, wherein the chloride test apparatus comprises an HCl chloride test apparatus, a catalytic organo chloride (RCl) conversion means containing a catalyst, and an HCl equivalents chloride test apparatus.

2. The system of claim 1, wherein the sample port further comprises a restriction valve.

3. The system of claim 1, wherein the sample port further comprises a needle valve.

4. The system of claim 1, wherein the sample port further comprises a vent.

5. The system of claim 1, wherein the catalytic RCl conversion means and HCl equivalents chloride test apparatus are arranged in series.

6. The system of claim 1, further comprising a pump or aspirator.

7. The system of claim 1, further comprising a dehumidifier.

8. A method for in situ measuring the total chloride content of a process product stream sample, employing a system according to claim 1, comprising the steps of:
   1) removing a sample to be tested from a product stream to provide the product stream sample,
   2) analysing the product stream sample to measure the HCl content thereof,
   3) catalytically converting any RCl in said product stream sample to produce HCl equivalents,
   4) analysing the HCl equivalents produced in step 3) to measure the HCl equivalents content thereof, and
   5) calculating the total chloride content of the product stream sample based on the sum of the HCl and HCl equivalents content measurements of steps 2) and 4).

9. The method of claim 8, wherein the product stream is in the form of a gas or liquid.

10. The method of claim 8, comprising performing step 1) at any one or more of the following points in the process; after the introduction of a feedstock, or after a desalter, or after a Catalytic Reforming Unit (CRU), before or after a chloride guard, before or after any chloride-sensitive equipment, or before final product discharge or storage.

11. The method of claim 8, comprising performing step 1) via the sample port.

12. The method of claim 8, comprising recording the volume of the product stream sample being subjected to the test method.

13. The method of claim 8, wherein the method provides a quantitative measure of HCl content in the process product stream sample of between 0.05 ppmv and 50 ppmv.

14. The method of claim 8, wherein the method provides a quantitative measure of HCl equivalents in the process product stream sample between 0.05 ppmv and 50 ppmv.

15. The method of claim 8 comprising the following steps:
   i) attaching the chloride test apparatus to the connector,
   ii) removing a sample to be tested from a product stream to provide a product stream sample via said sample port comprising the step of opening the isolation valve, and subsequently closing the isolation valve once the product stream sample has been removed,
   iii) analysing the product stream sample to measure the HCl content thereof,
   iv) catalytically converting any RCl in said product stream sample to produce HCl equivalents,
   v) analysing the HCl equivalents produced in step iv) to measure the HCl equivalents content of the RCl content in the sample, and
   vi) calculating a total chloride content based on the sum of the HCl and HCl equivalents content measurements of steps iii and v to provide a total chloride content measurement.

16. The method of claim 8, wherein the method steps 1) to 5) are performed in series on a single product stream sample.

17. The method of claim 8, wherein the method is performed on the product stream sample at a pressure not exceeding 100 bar G.

18. The method of claim 8, comprising reducing the pressure of the product stream sample to ambient pressure.

19. The method of claim 8, comprising passing the product stream sample through a dehumidifier.

* * * * *